(12) United States Patent
McNair

(10) Patent No.: US 7,617,115 B2
(45) Date of Patent: Nov. 10, 2009

(54) SYSTEM AND METHOD FOR RISK-ADJUSTING INDICATORS OF ACCESS AND UTILIZATION BASED ON METRICS OF DISTANCE AND TIME

(75) Inventor: Douglas S. McNair, Leawood, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 414 days.

(21) Appl. No.: 10/751,820

(22) Filed: Jan. 5, 2004

(65) Prior Publication Data

US 2004/0193451 A1   Sep. 30, 2004

Related U.S. Application Data

(60) Provisional application No. 60/446,692, filed on Feb. 11, 2003.

(51) Int. Cl.
*G06F 19/00*  (2006.01)
*G06Q 10/00*  (2006.01)

(52) U.S. Cl. .............................. 705/3; 705/2
(58) Field of Classification Search ................ 705/2–3
See application file for complete search history.

(56) References Cited

U.S. PATENT DOCUMENTS

| | | | | |
|---|---|---|---|---|
| 5,420,786 | A * | 5/1995 | Felthauser et al. | 705/2 |
| 5,557,514 | A * | 9/1996 | Seare et al. | 705/2 |
| 5,918,208 | A * | 6/1999 | Javitt | 705/2 |
| 6,139,494 | A * | 10/2000 | Cairnes | 600/300 |
| 2003/0018633 | A1 * | 1/2003 | Horn | 707/4 |

OTHER PUBLICATIONS

Ashton et al., Geographic Variations in Utilization Rates in Veterans Affairs Hospitals and Clinics, Jan. 7, 1999, The New England Journal of Medicine, 340:32-39.*
Ashton et al., Hospital Use and Survival among Veterans Affairs Beneficiaries, Oct. 23, 2003, The New England Journal of Medicine, 349: 1637-1646.*
Wennberg, Understanding Geographic Variations in Health Care Delivery, Jan. 7, 1999, The New England Journal of Medicine, 340: 52-53.*

(Continued)

*Primary Examiner*—C. Luke Gilligan
*Assistant Examiner*—Tran Nguyen
(74) *Attorney, Agent, or Firm*—Shook, Hardy & Bacon L.L.P.

(57) ABSTRACT

A method and system suitable for automated adjustment of information represented in the transaction order records from clinical information systems of hospitals, clinics, and emergency rooms, in such a manner as to accurately reflect differences in access to care. Techniques from statistical processing are combined in a method that allows for optimization of the parameters such that statistical hypothesis testing using conventional parametric tests are valid and feasible, on account of close approximation to Gaussian normal distribution. The method and system is designed so as to be robust against wide variations in population density and transportation infrastructure, as reflects remote, rural, suburban, and metropolitan environments. Once optimized, the method and system can achieve reliable performance with regard to longitudinal measurement of health access indicators, which are used in planning and managing health services. The performance of this method and system is superior to predicate methods known to those skilled in the art.

1 Claim, 2 Drawing Sheets

OTHER PUBLICATIONS

Chan, Access to physicians in underserved communities in Canada: something old, something new, Nov. 2000, Proceedings 5th International Medical Workforce Conference, Australian Medical Workforce Advisory Committee and Commonwealth Department of Health and Aged Care, Sydney, 341.*

Weinert C, et al., MSU Rurality index: development and evaluation, Res I Nursing Health, 1995;18;453-64.*

Anderson TW, Darling DA; Asymptotic theory of certain goodness of fit criteria based on stochastic processes; Ann Math Stat; 1952;23:193:212.

Bindman AB, et al. Preventable hospitalizations and access to health care, JAMA, 1995;274(4):305-11.

Box GEP, Cox DR, An analysis of transformations, J Roy Stat Soc, Ser B., 1964;26:211-52.

Iezzoni Li, et al. Judging hospitals by severity-adjusted mortality rates: the influence of the severity-adjustment method, Am J Public Health, 1996:86(10)1379-87.

Iezzoni Li, The risks of risk adjustment, JAMA, 1997;278(19):1600-7.

Rosenthal GE, et al., A regional evaluation of variation in low-severity hospital admissions, J Gen Intern Med, 1997;12(7):416-22.

Silver MP, et al., Ambulatory care sensitive hospitalization rates in the aged medicare population: a rural-urban comparison, J Rural Health, 1997;13(4):285-94.

Snedecor GW, et al., Statistical Methods, 8e., Ames:Iowa Press, 1989, p. 293-5.

Weinert C, et al., MSU Rurality index: development and evaluation, Res Nursing Health, 1995;18;453-64.

* cited by examiner

SYSTEM AND METHOD FOR RISK-ADJUSTING INDICATORS OF ACCESS AND UTILIZATION BASED ON METRICS OF DISTANCE AND TIME

CROSS-REFERENCE TO RELATED APPLICATIONS

The application claims the benefit of U.S. Provisional Application No. 60/446,692, filed Feb. 11, 2003.

STATEMENT REGARDING FEDERALLY SPONSORED RESEARCH OR DEVELOPMENT

Not applicable.

TECHNICAL FIELD

The present invention relates to a system and method for risk-adjusting indicators of access and utilization of health care services based on metrics of distance, which may be either in terms of geographic distance or time

BACKGROUND OF THE INVENTION

Prevention is an important role for all health care providers. Providers can help individuals stay healthy by preventing disease, and they can prevent complications of existing disease by helping patients live with their illnesses. To fulfill this role, however, providers need data on the impact of their services and the opportunity to compare these data over time or across communities. Local, State, and Federal policymakers also need these tools and data to identify potential access or quality-of-care problems related to prevention, to plan specific interventions, and to evaluate how well these interventions meet the goals of preventing illness and disability.

Quality indicators may be a set of measures that can be used with health system encounter data to identify "ambulatory care sensitive conditions" (ACSCs). ACSCs are conditions for which good outpatient care can potentially prevent the need for hospitalization, or for which early intervention can prevent complications or more severe disease.

Even though these indicators are based on hospital inpatient data, they provide insight into the quality of the health care system outside the hospital setting. Patients with newly diagnosed cancer may have poor survival or quality of life if their cancer management (chemotherapy, radiotherapy, etc.) is delayed more than a few weeks following diagnosis. Patients with diabetes may be hospitalized for diabetic complications if their conditions are not adequately monitored or if they do not receive the patient education needed for appropriate self-management. Patients may be hospitalized for asthma if primary care providers fail to adhere to practice guidelines or to prescribe appropriate treatments. Patients with appendicitis who do not have ready access to surgical evaluation may experience delays in receiving needed care, which can result in a life-threatening condition—perforated appendix.

SUMMARY OF THE INVENTION

The present invention relates to a system and method for risk-adjusting indicators of access and utilization of health care services based on metrics of distance, which may be either in terms of geographic distance or time. The risk-adjusted indicators are useful for determining the adequacy of access to care services within populations of varying rurality and managing resources related to high-quality provision of care services in metropolitan, suburban, and rural areas.

Indicators addressed by the present invention include (but are not limited to) the following ambulatory care sensitive conditions, which are measured as rates of encounter with the health system, regardless, of the point of origination of the episode that generates the encounter.

| | |
|---|---|
| Bacterial pneumonia | Hypertension |
| Dehydration | Adult asthma |
| Pediatric gastroenteritis | Pediatric asthma |
| Urinary tract infection | Chronic obstructive pulmonary disease (COPD) |
| Perforated appendix | Diabetes short-term complication |
| Low birth weight | Diabetes long-term complication |
| New cancer mgt delay > 14 days s/p initial dx or treatment | Uncontrolled diabetes |
| Congestive heart failure (CHF) | Lower-extremity amputation among patients with diabetes |

Although other factors outside the direct control of the health care system, such as poor environmental conditions or lack of patient adherence to treatment recommendations, can result in hospitalization, the indicators provide a meaningful starting point for assessing quality of health services in the community. Because the risk-adjusted indicators are calculated using readily available health system data, they are an easy-to-use and inexpensive screening tool. They can be used to provide a window into the community—to identify underserved or under-resourced community heath care needs, to monitor how well complications from a number of common conditions are being avoided in the outpatient setting, and to compare performance of local health care systems across communities.

Properly risk-adjusted indicators assess the quality of the health care system as a whole, and especially the quality of ambulatory care, in preventing medical complications. As a result, these measures are likely to be of the greatest value when calculated at the population level and when used by public health groups, data warehousing organizations, and other organizations concerned with the health of populations.

These indicators serve as a screening tool rather than as definitive measures of quality problems. They can provide initial information about potential problems in the community that may require further, more in-depth analysis. Policy makers and health care providers can use the risk-adjusted indicators to answer questions such as:

How does the low birth weight rate in my locale compare with the national average?

What can the rate of new cancer management encounters exceeding fourteen days tell me about the adequacy of oncology care in my community?

Does the admission rate for diabetes complications in my community suggest a problem in the provision of appropriate outpatient care to this population?

How does the admission rate for congestive heart failure vary over time and from one region of the country to another?

Government policy makers and local community organizations can use the indicators to assess and improve community health care. In order to do so in a valid and reliable manner, the indicators must generally be confirmed to have adequate precision and accuracy, and the indicators must be risk-adjusted to correct for variations in age and distance from access to care.

Access to various types of care services and treatments will vary for people living in the same county. Furthermore, a considerable number of care episodes (encounters with the health system) may begin when the person is at work or at locations other than their residence. For evaluation and planning purposes, health systems and public health services need to be able to measure access to care and quality of availability of care regardless of where geographically care episodes begin. The distance index and model of the present invention can be used for econometrics and clinical process consulting work with health care organizations in various countries and in various regions within any country, irrespective of the locale's rurality and regardless of how much of the health care provided by institutions in that locale is delivered to persons whose episodes of care originated outside the nominal catchment area for that locale's health jurisdiction. The distance index set forth in the present invention can utilize distance either measured in miles (kilometers) or elapsed-time minutes from the inception of a clinical event or need for care, until the provision of care at an appropriate location of service. (The minutes or geographical distance are statistical distributions, measurable and aggregated, in preferred embodiments, on a monthly or quarterly basis, from cases accruing in each catchment area.)

A preferred embodiment of the present invention for the United Kingdom uses the "Postcode District" (or PD), or, in another preferred embodiment for the United States, the present invention uses the 3-digit zip code or county FIPS (Federal Information Processing Standards) to identify geographic localities from which the captured cases originated. In the preferred embodiment for the U.K., the originating geographic locality is not identified with respect to the SHA and Hospital Trust geographic boundaries, which are not where the people live nor where the care episodes start out necessarily. The PD is the first part of a U.K. Postcode before the space in the Postcode and typically comprises two to four characters. It is used to specify the town or district to which a letter or package is to be sent for further sorting. Once the PD is received, the present invention obtains the census population and latitude-longitude GIS (Geographic Information System) coordinates for the centroid of each PD.

As known in the art, distance (or rurality) indexes suffer from three major difficulties, with regard to the purpose of risk-adjusting metrics denoting access to health services:

Failure to accurately and fully represent the continuum from rural to suburban to metropolitan, from fewer than one person per square kilometer to many hundreds or thousands of persons per square kilometer; from less than five minutes to access care to many hours or even days to access care for certain specialty services.

"Lumping" or assignment of a county-level distance index to all individuals living in a particular jurisdiction, which inaccurately represents the fine structure of access within the jurisdiction.

"Aggregation" and "norming" to macro sociopolitical levels (national or other), which obscures detailed small-area variation in access and composition of groups under study and prevents interpretation of differences among these groups.

The distance index described in the present invention avoids these pitfalls. First, by using resident-level case data the resulting index differentiates accurately between different locales within a county. Only two variables are required for each locale, one from each of the two following categories:

P: county population, or county population density.

D: distance in miles or kilometers, or distance in elapsed-minutes.

The method for calculating the distance index described herein further provides for automatic calculation of optimal parameters for a power transform, such that approximate normality for the purpose of statistical inferencing is achieved.

For each care episode and the person or family to which it pertains, a power transform is used for both the P-variable of the locale in which the episode originates, and for the D-variable. In the present invention, the Box-Cox transform involves iterative determination of optimal values for $\lambda_1$, the power to which each $D_i$ for the $i^{th}$ care episode is raised, and $\lambda_2$, the power to which each $P_i$ for the $i^{th}$ county or catchment area is raised. The transformation is expressed as:

$$D_i = \text{sign}(\lambda_1) \frac{D_i^{\lambda_1}}{std(D^{\lambda_1})}$$

$$P_i = \text{sign}(\lambda_2) \frac{P_i^{\lambda_2}}{std(P^{\lambda_2})}$$

where std $(P^{\lambda_2})$ is the sample standard deviation of $P_1^{\lambda_2}, \ldots, P_\lambda^{\lambda_2}$ and similarly for $D_i^{\lambda_1}$.

Next, the transformed values are scaled by the standard deviations, resulting in standardized values:

$$D_i = \text{sign}(\lambda_1) D_i^{\lambda_1}$$

$$P_i = \text{sign}(\lambda_2) P_i^{\lambda_2}$$

where $$\text{sign}(\lambda_j) = \begin{cases} +1 & \text{if } \lambda_j \geq 0 \\ -1 & \text{otherwise} \end{cases}$$

Then the two measures in each distance and population pair are weighted and summed to produce an intermediate provisional distance index. The distance metric is given a positive weight to ensure that the index will increase with increasing distance from the source of care services. And the population metric is given a negative weight to insure that the index will decrease as population or population density increase. Using the weighting in the preferred embodiment, the distance index for the $i^{th}$ episode is denoted $I_i$:

$$I_i = \left(\frac{1}{2}\right)\left[\text{sign}(\lambda_1)\frac{D_i^{\lambda_1}}{std(D^{\lambda_1})}\right] - \left[\text{sign}(\lambda_2)\frac{P_i^{\lambda_2}}{std(P^{\lambda_2})}\right]$$

The $I_i$ values are standardized, producing a scaled distance index for the $i^{th}$ episode:

$$d\_episode(i) = \frac{I_i - \text{mean}(I)}{std(I)}$$

The Anderson-Darling metric is calculated for the distribution of distance values, to assess departure from a normal curve, and if the value of $A_n^2$ is greater than or equal to $A_{n,\alpha}^2$ then the null hypothesis of normality is rejected and values of $\lambda_1$ and $\lambda_2$ are incremented and the loop processing is repeated. Iterations continue until $A_n^2$ is less than $A_{n,\alpha}^2$.

Risk-adjustment of indicator incidence rates may follow any of the methods known to those experienced in the art. The risk-adjustment must then be validated according to accepted statistical practices before interpretations and conclusions are drawn, or before the optimized values for $\lambda_1$ and $\lambda_2$ are deployed in a public health decision support software system.

The first step in the validation involves precision tests to determine the reliability of the indicator for distinguishing real differences in provider performance. For indicators that may be used for quality improvement, it is important to know with what precision, or surety, a measure can be attributed to an actual construct rather than random variation.

For each indicator, the variance can be broken down into three components: variation within a provider (actual differences in performance due to differing patient characteristics), variation among providers (actual differences in performance among providers), and random variation. An ideal indicator would have a substantial amount of the variance explained by between-area or between-provider variance, possibly resulting from differences in quality of care access, and a minimum amount of random variation. In the preferred embodiment, four tests of precision are used to estimate the magnitude of between-provider variance on each indicator:

Signal standard deviation is used to measure the extent to which performance of the indicator varies systematically across hospitals or areas.

Provider/area variation share is used to calculate the percentage of signal (or true) variance relative to the total variance of the indicator.

Signal-to-noise ratio is used to measure the percentage of the apparent variation in indicators across providers that is truly related to systematic differences across providers and not random variations (noise) from year to year.

In-sample R-squared is used to identify the incremental benefit of applying multivariate signal extraction methods for identifying additional signal on top of the signal-to-noise ratio.

In general, random variation is most problematic when there are relatively few observations per provider, when adverse outcome rates are relatively low, and when providers have little control over patient outcomes or variation in important processes of care is minimal. If a large number of patient factors that are difficult to observe influence whether or not a patient has an adverse outcome, it may be difficult to separate the "quality signal" from the noise in which it is embedded. Two techniques are applied to improve the precision of an indicator:

Univariate methods are used to estimate the "true" quality signal of an indicator based on information from the specific indicator and one year of data.

Multivariate signal extraction (MSX) methods are used to estimate the "true" quality signal based on information from a set of indicators and multiple years of data. In most cases, MSX methods extracted additional signal, which provided much more precise estimates of true hospital or area quality.

To determine the sensitivity of potential indicators to bias from differences in patient severity, unadjusted performance measures-for specific hospitals were compared with performance measures that had been adjusted for age and dcat with dcat derived from transformed distance between the origin location of the episode and the care service venue where the episode was consummated, or from which resources were dispatched in the case of patients treated in situ. Five empirical tests were performed to investigate the degree of bias in an indicator:

Rank correlation coefficient of the area or hospital with (and without) risk adjustment—gives the overall impact of risk adjustment on relative provider or area performance.

Average absolute value of change relative to mean—highlights the amount of absolute change in performance, without reference to other providers' performance.

Percentage of highly ranked hospitals that remain in high decile—reports the percentage of hospitals or areas that are in the highest deciles without risk adjustment that remain there after risk adjustment is performed.

Percentage of lowly ranked hospitals that remain in low decile—reports the percentage of hospitals or areas that are in the lowest deciles without risk adjustment that remain there after risk adjustment is performed.

Percentage that change more than two deciles—identifies the percentage of hospitals whose relative rank changes by a substantial percentage (more than 20%) with and without risk adjustment.

Despite the unique strengths of the indicators, there are several issues that should be considered when using these indicators. First, for some indicators, differences in socioeconomic status have been shown to explain a substantial part—perhaps most—of the variation in indicator rates across areas. The complexity of the relationship between socioeconomic status and indicator rates makes it difficult to delineate how much of the observed relationships are due to true access to care difficulties in potentially underserved populations, or due to other patient characteristics, unrelated to quality of care, that vary systematically by socioeconomic status. For some of the indicators, patient preferences and hospital capabilities for inpatient or outpatient care might explain variations in hospitalizations. In addition, environmental conditions that are not under the direct control of the health care system can substantially influence some of the indicators. For example, the Chronis Obstruction Pulmonary Disease (COPD) and asthma admission rates are likely to be higher in areas with poor air quality.

Second, the evidence related to potentially avoidable hospital admissions is limited for each indicator, because many indicators have been developed as parts of sets. Only a few studies have attempted to validate individual indicators rather than whole measure sets. Weissman J S. Rates of avoidable hospitalization by insurance status. *JAMA*. 1992; 268:2388-94; Bindman A B. Preventable hospitalizations and access to healthcare. *JAMA*. 1995; 274:305-11; Silver M P. Ambulatory care sensitive hospitalization rates in the aged Medicare population in Utah: a rural-urban comparison. *J Rural Health*. 1997; 13:285-94.

"Raw" unadjusted measures of hospital or area performance for each indicator are simple means constructed from the encounter data and census population counts. Simple means do not account for differences in the indicators that are attributable to differences in patient mix across hospitals that are measured in the encounter data, or demographic differences across areas. In general, risk adjustment involves conducting a multivariate regression to adjust expected performance for these measured patient and population characteristics. Although complex, multivariate regression methods are the standard technique for risk-adjustment because they permit the simultaneous consideration of multiple patient characteristics and interaction among those characteristics. The interpretation of the risk-adjusted estimate is straightforward: it is the value of the indicator expected at that hospital if the hospital had an "average" patient case-mix.

Empirical performance: discrimination. A critical aspect of the performance of a risk-adjustment model is the extent to which the model predicts a higher probability of an event for patients who actually experience the event. The statistical test of discrimination is generally expressed as a C-statistic or $R^2$ (how much of the variation in the patient level data the model explains). In general, systems that discriminate more have the potential to influence indicator measures more substantially. Many severity-adjustment systems were designed primarily to predict in subsequent periods (e.g., resource consumption next year). However, for purposes of evaluating access indicator performance, the estimation of concurrent risk is more important (i.e., differences in the likelihood of a beneficiary's obtaining access and appropriately utilizing services to which she/he is eligible in the current time period). Ideally, discrimination is assessed using $R^2$ or other statistic of predicted variation that is computed on a separate data source from the one used to develop the model, and to avoid "over-fitting" (i.e., the model might appear to do well in part because it explains nonsystematic variations in the data used to develop the model).

Calibration is also an important component of validation. Calibration is a measure of whether the mean of the predicted outcomes equals the mean of the actual outcomes for the entire population and for population subgroups. The statistical test is often expressed as a Chi-square or "goodness-of-fit" for the equivalence of means of population subgroups. Even if the severity-adjustment system does not predict well at the level of individuals, it may predict well at the aggregate (group) level of, say, women, 70-74 years of age. Over-fitting is an issue as well, unless a different data source is used to validate the model than was used to estimate the model.

Risk-adjustment is implemented using patient care episode demographics (age and dcat). Then statistical methods are used to account for additional sources of noise and bias not accounted for by observed patient characteristics. By applying these methods to the indicators, the relative importance of both risk adjustment and smoothing can be evaluated in terms of the relative performance of hospitals (or areas) compared to the "raw" unadjusted indicators based on simple means from encounter data. In general, simple means fail to account both for differences in the indicators that are attributable to systematic differences in measured and unmeasured patient mix across hospitals/areas that are measured in the discharge data, and for random variations in patient mix. A multivariate regression approach adjusts performance measures for measured differences in patient mix and permits the inclusion of multiple patient demographic and severity characteristics.

Specifically, if it is denoted whether or not the event associated with a particular indicator $Y^k$ (k=1, ..., K) was observed for a particular patient i at hospital/area j (j=1, ..., J) in year t (t=1, ..., T), then the regression to construct a risk-adjusted "raw" estimate a hospital or area's performance on each indicator can be written as:

$$Y^k_{ijt}=M^k_{jt}+Z_{ijt}\Pi^k_t+\epsilon^k_{ijt}, \text{ where} \quad (1)$$

$Y^k_{ijt}$ is the $k^{th}$ quality indicator for patient i discharged from hospital/area j in year t (i.e., whether or not the event associated with the indicator occurred on that discharge);

$M^k_{jt}$ is the "raw" adjusted measure for indicator k for hospital/area j in year t (i.e., the hospital/area "fixed effect" in the patient-level regression);

$Z_{ijt}$ is a vector of patient covariates for patient i discharged from hospital/area j in year t (i.e., the patient-level measures used as risk adjusters);

$\Pi^k_t$ is a vector of parameters in each year t, giving the effect of each patient risk adjuster on indicator k (i.e., the magnitude of the risk adjustment associated with each patient measure); and $\epsilon^k_{ijt}$ is the unexplained residual in this patient-level model.

The hospital or area specific intercept $M^k_{jt}$ is the "raw" adjusted measure of a hospital or area's performance on the indicator, holding patient covariates constant. In most of the empirical analysis that follows, the patient-level analysis is conducted using data from all hospitals and areas. (The model shown implies that each hospital or area has data for all years, and with each year has data on all outcomes; however, this is not essential to apply risk adjustment methods.)

These patient-level regressions are estimated by linear ordinary least-squares (OLS). In general, the dependent variables in the regressions are dichotomous, which raises the question of whether a method for binary dependent variables such as logit or probit estimation might be more appropriate. OLS regression has been successfully used for similar analyses of hospital/area differences in outcomes. In addition, estimating logit or probit models with hospital or area fixed effects cannot be done with standard methods; it requires computationally intensive conditional maximum likelihood methods that are not easily extended to multiple years and multiple measures.

A commonly used solution to this problem is to estimate a logit model without hospital or area effects, and then to use the resulting predictions as estimates of the expected indicator. However, this method yields biased estimates and predictions of health system performance. In contrast, it is easy to incorporate hospital or area fixed effects into OLS regression analysis. The resulting estimates are not biased, and the hospital or area fixed effects provide direct and easily-interpretable estimates of the outcome rate for a particular hospital or area measure in a particular year, holding constant all observed patient characteristics.

A potential limitation of the OLS approach is that it may yield biased estimates of confidence intervals, because the errors of a linear probability model are necessarily heteroskedastic. Given the large sample sizes for the parameters estimated from these regressions (most indicators involve thousands of "denominator" encounters per year), such statistical efficiency is not likely to be an important concern. Nevertheless, models are estimated using Weighted Least Squares to account for heteroskedasticity, in a manner familiar to those skilled in the art, to see if estimates were affected. Very similar estimates of adjusted indicator performance were obtained.

Specifically, in addition to age, distance category, and age*dcat interactions as adjusters, the model also included. For each hospital, a vector of K adjusted indicator estimates is observed over T years from estimating the patient-level regressions (1) run separately by year for each indicator. Each indicator is a noisy estimate of true health system quality in each area.

In particular, let $M_j$ be the 1×TK vector of estimated indicator performance for hospital j. Then:

$$M_j=\mu_j+\epsilon_j \quad (2)$$

Where $\mu_j$ is a 1×TK vector of the true hospital intercepts for hospital j, and $\epsilon_j$ is the estimation error (which has a mean zero and is uncorrelated with $\mu_j$). Note that the variance of $\epsilon_j$ can be estimated from the patient-level regressions, since this is simply the variance of the regression estimates $M_j$. In particular, $E(\epsilon_{jt}' \epsilon_{jt})=\Omega_{jt}$ and $E(\epsilon_{jt}' \epsilon_{js})=0$ for $t \neq s$, where $\Omega_{jt}$ is the covariance matrix of the intercept estimates for hospital j in year t.

A linear combination of each hospital's observed indicators must be created in such a way that it minimizes the mean-squared prediction error. Thus, the following regression is run:

$$\mu_{jt}^k = M_j \beta_{jt}^k + v_{jt}^k \quad (3)$$

but cannot be run directly, since $\mu$ is unobserved and the optimal $\beta$ varies by hospital and year. While equation (3) cannot be directly estimated, it is possible to estimate the parameters for this hypothetical regression. In general, the minimum mean squared error linear predictor of $\mu$ is given by $M_j\beta$, where $\beta=[E(M_j'M_j)]^{-1}E(M_j'\mu_j)$. This best linear predictor depends on two moment matrices:

$$E(M_j'M_j)=E(\mu_j'\mu_j)+E(\epsilon_j'\epsilon_j) \quad (4.1)$$

$$E(M_j'\mu_j)=E(\mu_j'\mu_j) \quad (4.2)$$

The required moment matrices are estimated directly as follows:

Estimate $E(\epsilon_j' \epsilon_j)$ with the patient-level OLS estimate of the covariance matrix for the parameter estimates $M_j$. Call this estimate $S_j$. Note that $S_j$ varies across hospitals.

Estimate $E(\mu_j' \mu_j)$ by noting that $E(M_j'M_j-S_j)=E(\mu_j' \mu_j)$. If we assume that $E(\mu_j' \mu_j)$ is the same for all hospitals, then it can be estimated by the sample average of $M_j'M_j-S_j$. Note that it is easy to relax the assumption that $E(\mu_j' \mu_j)$ is the same for all hospitals by calculating $M_j'M_j-S_j$ for subgroups of hospitals.

With estimates of $E(\mu_j' \mu_j)$ and $E(\epsilon_j' \epsilon_j)$, one can form least squares estimates of the parameters in equation (3) which minimize the mean squared error. Analogous to simple regression, the prediction of a hospital's true intercepts is given by:

$$M_j E(M_j'M_j)^{-1} E(M_j'\mu_j) = M_j [E(\mu_j'\mu_j)+E(\epsilon_j'\epsilon_j)]^{-1} E(\mu_j'\mu_j) \hat{\mu}_j \quad (5)$$

using estimates of $E(\mu_j' \mu_j)$ and $E(\epsilon_j' \epsilon_j)$ in place of their true values. One can use the estimated moments to calculate other statistics of interest as well, such as the standard error of the prediction and the r-squared for equation (3), based on the usual least squares formulas. Estimates based on equation (5) are referred to as "filtered" estimates, since the key advantage of such estimates is that they optimally filter out the estimation error in the raw quality indicators.

Equation (5) in combination with estimates of the required moment matrices provides the basis for estimates of hospital quality or health service area quality with regard to care access. Such estimates of hospital quality have a number of attractive properties. First, they incorporate information in a systematic way from many outcome indicators and many years into the predictions of any one outcome. Moreover, if the moment matrices were known, the estimates of hospital quality represent the optimal linear predictors, based on a mean squared error criterion. Finally, these estimates maintain many of the attractive aspects of existing Bayesian approaches, while dramatically simplifying the complexity of the estimation. It is possible to construct univariate smoothed estimates of hospital quality, based only on empirical estimates for particular measures, using the models just described but restricting the dimension of $M_j$ to only a particular indicator k and time period t. Of course, to the extent that the provider indicators are correlated with each other and over time, this will result in a less precise estimate.

With the system and method applied over time with multiple years of data accruing longitudinally, it is advantageous to impose structure on $E(\mu_j'\mu_j)$ for two reasons. First, this improves the precision of the estimated moments by limiting the number of parameters that need to be estimated. Second, a time series structure allows for out-of-sample forecasts. A non-stationary, first-order Vector Autoregression structure. (VAR) is used. The VAR model is a generalization of the usual autoregressive model, and assumes that each hospital's quality indicators in a given year depend on the hospital's quality indicators in past years plus a contemporaneous shock that may be correlated across quality indicators. In most of what follows, a non-stationary first-order VAR is assumed for $\mu_{jt}$ (1×K), where:

$$\mu_{jt}=\mu_{j,t-1}\Phi+u_{jt}, \text{ with } V(u_{jt})=\Sigma \text{ and } V(\mu_{j1})=\Gamma. \quad (6)$$

Thus, estimates are needed of the lag coefficient ($\Phi$), the variance matrix of the innovations ($\Sigma$), and the initial variance condition ($\Gamma$), where $\Sigma$ and $\Gamma$ are symmetric K×K matrices of parameters and $\Phi$ is a general K×K matrix of parameters, for a total of $2K^2+K$ parameters. For example, ten parameters must be estimated for a VAR model with two outcomes (K=2).

The VAR structure implies that $E(M_j'M_j-S_j)=E(\mu_j'\mu_j)=f(\Phi, \Sigma, \Gamma)$. Thus, the VAR parameters can be estimated by Optimal Minimum Distance (OMD) methods, i.e., by choosing the VAR parameters so that the theoretical moment matrix, $f(\Phi, \Sigma, \Gamma)$, is as close as possible to the corresponding sample moments from the sample average of $M_j'M_j-S_j$. More specifically, let $d_j$ be a vector of the non-redundant (lower triangular) elements of $M_j'M_j-S_j$, and let $\delta$ be a vector of the corresponding moments from the true moment matrix, so that $\delta=g(\Phi,\Sigma,\Gamma)$. Then the OMD estimates of $(\Phi,\Sigma,\Gamma)$ minimize the following OMD objective function:

$$M[d-g(\Phi,\Sigma,\Gamma)]'V^{-1}[d-g(\Phi,\Sigma,\Gamma)]q \quad (7)$$

where V is the sample estimate of the covariance matrix for d, and D is the sample average of d. If the VAR model is correct, the value of the objective function, q, will be distributed $\chi^2(p)$ where p is the degree of over-identification (the difference between the number of elements in d and the number of parameters being estimated). Thus, q provides a goodness of fit statistic that indicates how well the VAR model fits the actual covariances in the data.

Finally, estimated $R^2$ statistics are used to evaluate the filtered estimates' ability to predict (in sample) and forecast (out-of-sample) variation in the true intercepts, and to compare methods used to conventional methods (e.g., simple averages, or univariate shrinkage estimators). If true hospital intercepts ($\mu$) were observed, a natural metric for evaluating the predictions would be the sample R-squared:

$$R^2 = 1-(\Sigma_{j=1}^N \hat{\mu}_j^2)/(\Sigma_{j=1}^N \mu_j^2) \quad (8)$$

where $$\hat{\mu}_j = \mu_j - \hat{\mu}_j$$

is the prediction error. Of course $\mu$ is not observed. Therefore, an estimate is constructed using the estimate of $E(\mu_j' \mu_j)$ for the denominator, and the estimate of $$E[(\mu_j-\hat{\mu}_j)'(\mu_j-\hat{\mu}_j)]$$

for the terms in the numerator. Finally, a weighted R-squared is calculated (weighting by the number of patients treated by each hospital).

In accordance with the invention, a method and system mitigating the limitations enumerated above and suitable for a risk-adjustment procedure for correcting reported rates of health care utilization or access indicators are provided. The invention is intended to be used by health care organizations in monitoring and undertaking steps to correct or improve service delivery, or by units of government seeking to evaluate access.

Additional advantages and novel features of the invention will be set forth in part in a description which follows, and in part will become apparent to those skilled in the art upon examination of the following, or may be learned by practice of the invention.

BRIEF DESCRIPTION OF THE DRAWINGS

The present invention is described in detail below with reference to the attached drawing figures, wherein.

DETAILED DESCRIPTION OF THE INVENTION

Figure 1:
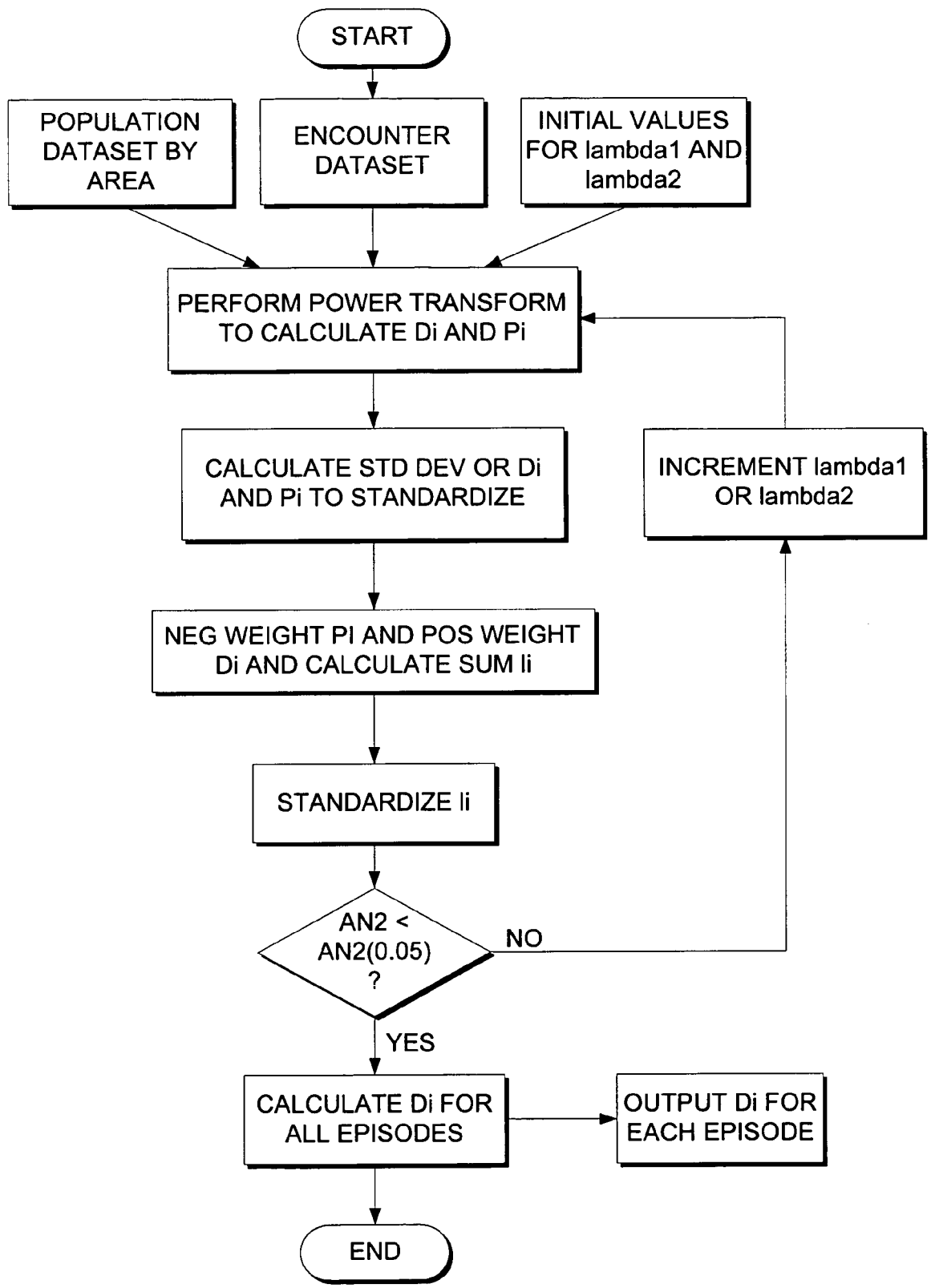
FIG. 1 is a flow chart illustrating a preferred method for developing, optimizing, and validating the locally normed transformed distances and populations, using the Anderson-Darling metric as a stopping criterion (alpha may in the preferred embodiment be selected by the user, but in most cases it will be p=0.05)

Referring now to FIG. 1, a diagram is shown of the elements comprising the method and system for generating the locally normed distance index and verifying and validating whether such an index achieves adequate goodness of fit in the intended geographic region of deployment, sufficient for satisfactory performance in the use for risk-adjusting indicators of access to and utilization of health services.

Figure 2:
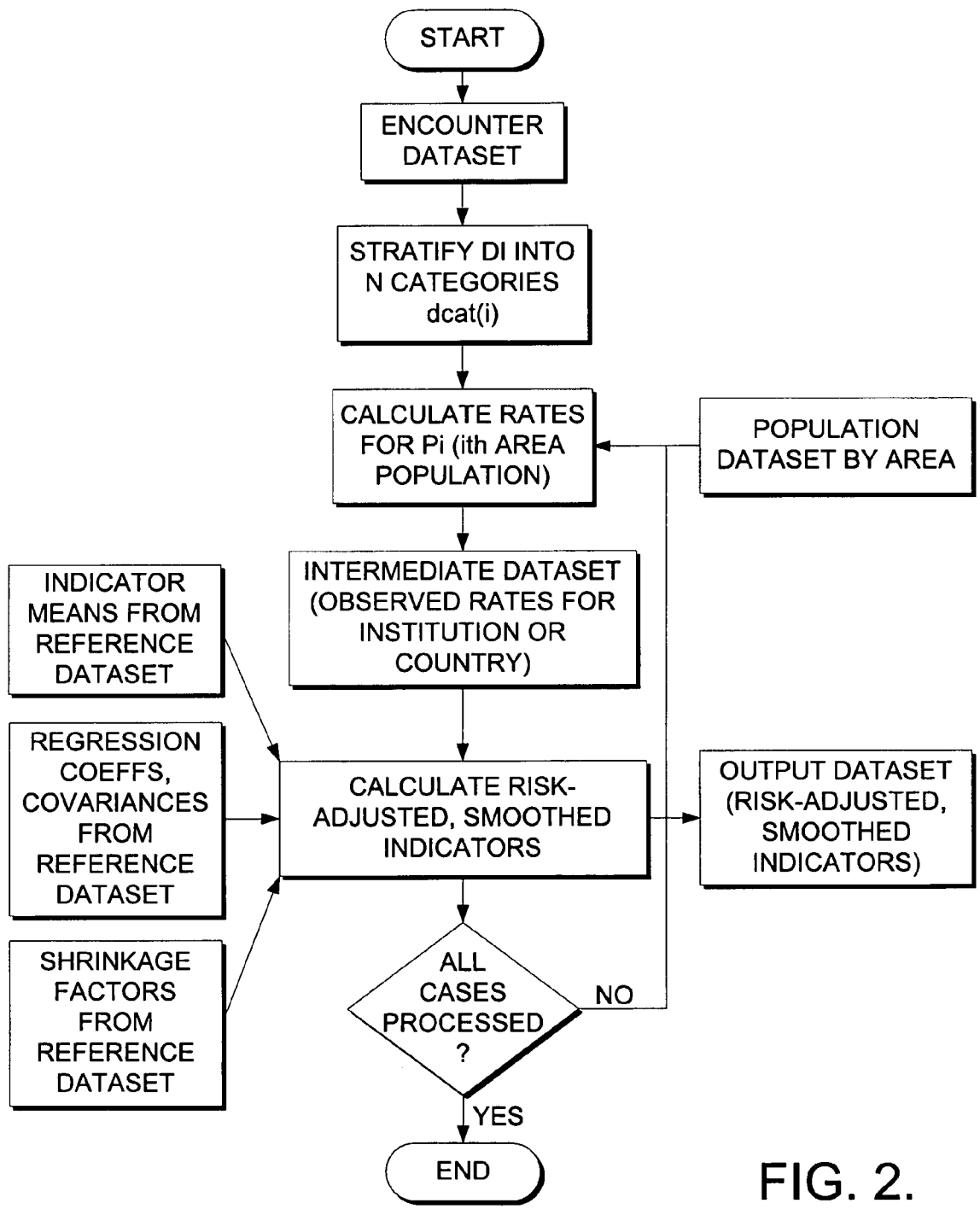
FIG. 2 is a flow chart illustrating an exemplary embodiment of a plurality of possible risk-adjustment embodiments, implementing the said method of FIG. 1.

Referring now to FIG. 2, a diagram is shown of the elements comprising the method and system for applying the locally normed distance index, stratified into a finite number of categories, to risk-adjust the incidence rates for access-related utilization indicators. The data element HOSPSTCO provides flexibility to calculate the indicators by hospital location or by patient residence. If the user wants to calculate the indicators using the population associated with the hospital location as the denominator, the values for this variable should be the individual hospital FIPS state/county codes. Calculating indicators based on the population of the MSA region or county associated with inception of each care episode, which may or may not be the locale in which the patient resides, the values for this variable should be the FIPS state/county code or PD associated with each individual location where a care episode commences.

If the hospital FIPS code is used in HOSPSTCO, rates may be biased for hospitals, which serve as regional referral centers. These hospitals are more likely to treat patients from outside the MSA, county or even the state in which the facility is located compared to hospitals that are not tertiary centers. Therefore, using the care episode origination FIPS state/county code for analysis more accurately reflects the true population at risk. Evaluation of geographic variations in admissions for ambulatory care sensitive conditions by episode FIPS or postcode district or zip code can result in better information to guide community or provider response.

It is possible that some records in the input data file may be missing the patient FIPS code. Any records with missing values in the HOSPSTCO data field are excluded from the calculations of observed, risk-adjusted and smoothed indicator rates.

A preferred embodiment of the present invention in SAS source code format and a sample data set are attached hereto as an exemplary means of implementing the present invention.

Although the invention has been described with reference to the preferred embodiment illustrated in the attached drawing figures, it is noted that substitutions may be made and equivalents employed herein without departing from the scope of the invention as recited in the claims. For example, additional steps may be added and steps omitted without departing from the scope of this invention.

What the invention claimed is:

1. Computer-storage media having computer-executable instructions embodied thereon that, when executed, cause a machine to perform a method for effecting a controlled, recurring assessment of a care episode and service utilization patterns associated with a locale, the locale including a plurality of corresponding institutions, the method comprising the steps of:
 (a) receiving a population dataset comprising one or more population data records, wherein each population data record describes a population or population density for a unique geographic location, and wherein none of the described geographic locations overlaps;
 (b) receiving an encounter dataset comprising one or more encounter data records, wherein each encounter data record describes a distance, measured in physical distance or time, between:
  (1) an inception of a clinical event or need for care; and
  (2) provision of care at an appropriate location of service;
 (c) receiving one or more statistical parameters;
 (d) for each population data record, statistically power transforming the data contained in the respective population data record using the one or more statistical parameters to generate a corresponding transformed population data record;
 (e) for each encounter data record, statistically power transforming the data contained in the respective encounter data record using the one or more statistical parameters to generate a corresponding transformed encounter data record;
 (f) for each transformed population data record, standardizing each transformed population data record using the set of all transformed population data records as a first baseline to generate a corresponding standardized transformed population data record;
 (g) for each transformed encounter data record, standardizing each transformed encounter data record using the set of all transformed encounter data records as a second baseline to generate a corresponding standardized transformed encounter data record;
 (h) linking each standardized transformed encounter data record to a corresponding standardized transformed population data record;
 (i) for each standardized transformed encounter data record, calculating a distance index based on the respective standardized transformed encounter data record and the corresponding standardized transformed population data record;
 (j) for each distance index, standardizing the respective distance index using the set of all distance indices as a third baseline to generate a standardized distance index;
 (k) assessing the departure of the set of one or more standardized distance indices from a standard normal statistical distribution;

(l) if the assessment in step (k) conforms to a predetermined threshold, identifying the set of standardized distance indices as the set of optimized distance indices;

(m) else if the assessment in step (k) does not conform to the predetermined threshold, changing the one or more statistical parameters and repeating steps (d-k);

(n) identifying one or more health care providers;

(o) for each optimized distance index, risk-adjusting the respective optimized distance index and assigning the risk-adjusted optimized distance index to a single health care provider chosen from the set of one or more health care providers based on the geographic location served by the health care provider; and (p) for each health care provider, generating a report by aggregating any risk-adjusted optimized distance indices assigned to the respective health care provider, wherein the report assesses for the corresponding geographic location served by the health care provider:

(1) quality of health services;

(2) under-resourced health care needs;

(3) prevention of medical complications; and (4) comparative performance of the corresponding health care providers to other health care providers.

* * * * *

UNITED STATES PATENT AND TRADEMARK OFFICE
CERTIFICATE OF CORRECTION

| | | |
|---|---|---|
| PATENT NO. | : 7,617,115 B2 | Page 1 of 1 |
| APPLICATION NO. | : 10/751820 | |
| DATED | : November 10, 2009 | |
| INVENTOR(S) | : Douglas S. McNair | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 777 days.

Signed and Sealed this

Nineteenth Day of October, 2010

David J. Kappos
*Director of the United States Patent and Trademark Office*